United States Patent [19]

Yamamoto et al.

[11] 4,404,524

[45] Sep. 13, 1983

[54] IONIZATION DETECTOR

[75] Inventors: Hajime Yamamoto, Hitachi; Yoshihiko Sato, Ibaraki, both of Japan

[73] Assignee: Hitachi, Ltd., Tokyo, Japan

[21] Appl. No.: 221,019

[22] Filed: Dec. 29, 1980

[30] Foreign Application Priority Data

Jan. 7, 1980 [JP] Japan ................ 55-113

[51] Int. Cl.$^3$ ............................................ G01N 27/62
[52] U.S. Cl. .................................... 324/459; 324/468
[58] Field of Search ............... 324/464, 468, 470, 459

[56] References Cited

U.S. PATENT DOCUMENTS 2,928,042 3/1960 Lawrance et al. ............... 324/468
4,117,396 9/1978 Berkey ............................ 324/468
4,282,741 8/1981 Zarchy ............................ 324/468

Primary Examiner—Michael J. Tokar
Attorney, Agent, or Firm—Antonelli, Terry & Wands

[57] ABSTRACT

An ionization detector which ionizes particles of a substance to be easily ionized and then measures the number of the ionized particles as ionization current. The detector comprises a heater for ionizing particles, a collector disposed opposite to the heater for collecting ionized particles, and a control arrangement for controlling the temperature of the heater to a constant value. Thus, by preventing the fluctuation of the temperature of the heater due to the fluctuations of the voltage of the power source and of the flow of a cooling fluid which is detected as the ionized particles, an exact measurement of the number or concentration of ionized particles can be performed.

7 Claims, 10 Drawing Figures

IONIZATION DETECTOR

BACKGROUND OF THE INVENTION

This invention relates to an ionization detector which ionizes matter to be detected, detects the resulting ionization current, and indicates the concentration of the matter on the basis of the detected ionization current.

In a fast breeder reactor, liquid metal having a high seat conductivity, such as liquified sodium, is used to cool the reactor core. The liquid sodium circulates through the reactor core by means of a piping system. During the circulation via the reactor core, there may be a little leakage of sodium vapor. To secure the safety of the reactor system, such leakage must be detected as soon as possible. For the detection of the leakage of sodium, the surrounding gas in the vicinity of every branch of the piping is sampled and the sampled gas is sent to a sodium ionization detector (also referred to as SID for brevity). In the SID, the sodium particles contained in the sampled gas are ionized by the heat generated by a filament and the generated $Na^+$ ions are collected by a collector. The number of the sodium particles can be detected by detecting the ionization current flowing between the filament and the collector. An ionization detector of this type is disclosed in the U.S. Pat. No. 4,117,396. According to that disclosure, the filament is always heated up to 800°–1000° C. so as to effectively ionize the sodium particles on the surface thereof. With the SID filament as disclosed in the above literature, the temperature of the filament fluctuates with the lapse of time, depending upon the changes in the flow of the gas to be sampled, the current sent through the filament to generate heat, etc. Accordingly, the ionization current also fluctuates so that it becomes difficult to exactly detect the number of the sodium particles.

Another apparatus for detecting the leakage of fluid such as, for example, liquified sodium is disclosed in the commonly assigned U.S. patent application Ser. No. 60,767 filed on July 26, 1979, now U.S. Pat. No. 4,259,861. In that apparatus, sodium leakage is detected on the basis of the phenomenon that when electrically conductive metal having a small heat capacity touches sodium in the state of mist, the temperature of the metal falls. The temperature of the electrically conductive metal is kept at a temperature through a feedback control. The change in the temperature of the metal causes the change in the electrical conductivity thereof and the latter is taken out as a pulse output. The pulse output thus obtained is subjected to a desired processing and thereafter sent to a pulse height analyzer to detect the concentration of the sodium mist. Therefore, this apparatus can make a rather exact determination of sodium leakage, but there is also need for a complicated circuit for processing the output pulse.

SUMMARY OF THE INVENTION

An object of this invention is to provide an ionization detector for exactly detecting the number of ionized particles.

Another object of this invention is to provide an ionization detector for exactly detecting the number of ionized particles by means of an apparatus having a simple structure.

According to this invention, there is provided an ionization detector comprising a heating means for ionizing the particles of substance to be detected, a collector electrode for collecting the ionized particles, a detecting means for applying a voltage between the heating means and an electrode opposite to the heating means and for detecting the ionization current based on the ionized particles, and a control means for controlling the temperature of the heating means.

As described in U.S. Pat. No. 4,117,396, if a voltage is applied between the anode and the filament, the particles ionized as a result of their contact with the filament then turn into ion current flowing into the anode. The ion current depends on the temperature of the filament and the relationship between the ion current and the filament temperature is non-linear. The present inventors have ascertained that the fluctuation of the flow of gas or the filament heating current largely affects the filament temperature. For example, when the filament is kept at temperatures higher than 800° C., the maximum fluctuation of the filament temperature is about ±50° C. It is therefore necessary to exactly control the filament temperature so as the measure the ionization current exactly.

This invention has been made on the basis of the above consideration and the number or the concentration of the ionized particles can be exactly detected, without using any complicated device, through the provision of a control means for controlling the temperature of the heating means such as filament for producing ionized particles.

DESCRIPTION OF THE PREFERRED EMBODIMENTS

Figure 1:
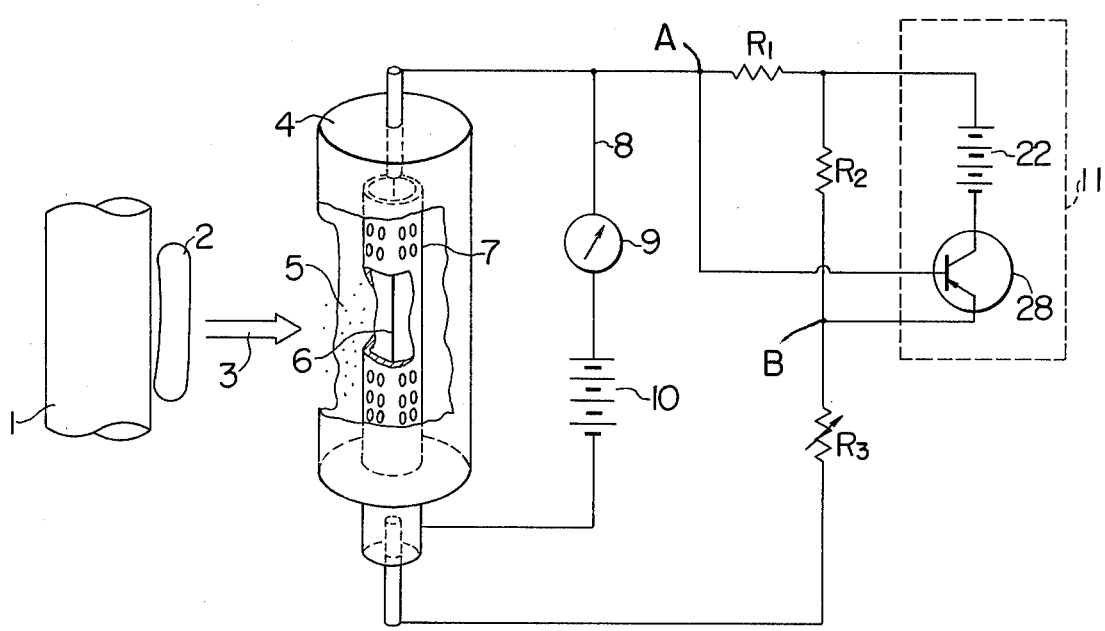
FIG. 1 schematically shows the general view of a detection system including an ionization detector as an embodiment of this invention.

In FIG. 1, a part of surrounding gas 2 is always sampled near a length of piping 1 and the sampled gas 3 is sent to a sodium ionization detector 4. In the sodium ionization detector 4, the sodium particles 5 contained in the sampled gas 3 are ionized by a filament 6. The thus produced $Na^+$ ions are collected by an anode, i.e. collector 7, so that the ionization current flowing in a circuit 8 is detected by a detector 9. The number of the sodium particles is detected on the basis of the detected current. A high voltage source (700 V) is connected between the collector 7 and the filament 6, to collect $Na^+$ ions. The filament 6, forming a resistor, and three resistors $R_1$, $R_2$ and $R_3$ constitute a bridge circuit. To balance the bridge circuit at the operating temperatures (above 800° C., e.g., about 1000° C.) of the filament 6, the values of the resistances of the resistors $R_1$, $R_2$ and $R_3$ are chosen as follows. The filament of the detector is made of platinum, having a diameter of about 0.3 mm and a length of about 60 mm. The electric resistance of the filament at 1000° C. is therefore 0.02 Ω. The value $R_1$ is first set approximately equal to the resistance of the filament (0.02 Ω). The value $R_2$ is set about 100 times as large as $R_2$ (i.e. 2 Ω). The value $R_3$ can be determined from the bridge balance condition such that $R_3=0.02\times R_2/R_1=2$ Ω, but preferably the resistor $R_3$ is a variable resistor covering 0–5 Ω. This variable resistor makes it possible to correct the deviations of the resistors so as to establish an exact balance in the bridge circuit or to change the operating temperature of the filament arbitrarily by changing the resistance value $R_3$ of the resistor, as described later.

The principle of temperature control is based on the utilization of the change in the electric resistance of the filament due to the change in the filament temperature. When the filament temperature falls as a result of some disturbance, the resistance of the filament decreases to cause the balanced condition of the bridge to collapse. Accordingly, a voltage or a potential difference Δe appears between points A and B, owing to the induced unbalance. This potential difference Δe is supplied to a current amplifier 11 and the current proportional to Δe is in turn fed back to the bridge circuit. The current amplifier 11 comprises a dc power source and an amplifier (i.e. power transistor) 28. The current fed back from the current amplifier 11 is then divided by the resistors $R_1$ and $R_2$. Since the resistance value (∼0.04 Ω) of the resistor $R_1$ is much lower than that (∼4 Ω) of the resistor $R_2$, most part of the feedback current flows through a circuit branch containing the resistor $R_1$ and the filament. This current causes the filament to generate heat. Accordingly, the temperature of the filament rises to increase the resistance of the filament, so that a condition near the previous balance condition is resumed. According to this embodiment, therefore, the filament temperature, which has shifted from the initially set value, is restored to the initial value in a short time by the current feedback control described above. In this case, the response time in control, i.e. the time from the instant when the filament temperature begins to change to the instant when the filament temperature is restored to the initial value, depends on the amplification factor μ of the power transistor 28. In the case of a power transistor purchasable on the market and having a value of μ equal to about 20,000, the response time is about 5 μsec.

Figure 2:
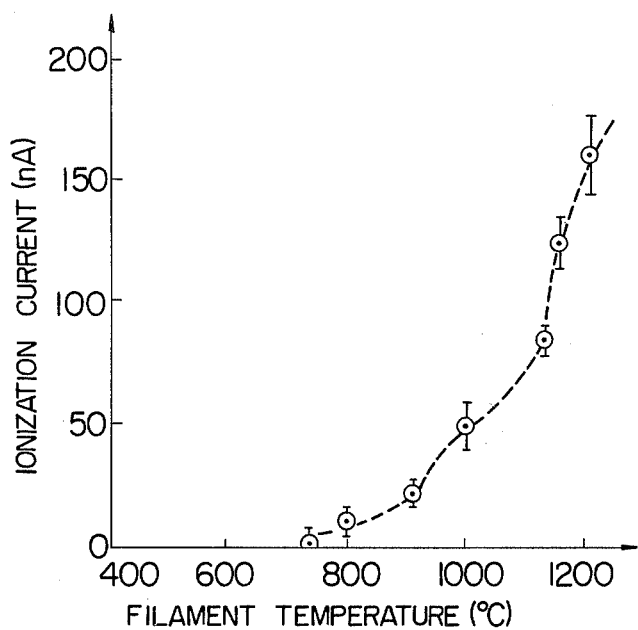
FIG. 2 shows the relationship between the ionization current and the filament temperature.

FIG. 2 shows the relationship between the filament temperature and the ionization current. To obtain this relationship, the filament was heated by an ac power source and the ionization current was measured without resorting to the temperature control means embodying this invention. The fluctuation of the ionization current at the operating filament temperature is due to the fluctuation of the filament temperature caused by the fluctuation of the current from the power source or of the flow of carrier gas. The present inventors have ascertained that the fluctuation of the filament temperature at the operating temperatures (higher than 800° C.) covers a range of −50°∼+50°C. Also, a non-linear relation is observed between the ionization current and the filament temperature. These facts suggest that it is necessary to keep the filament temperature constant by the use of a fast responsive control so as to exactly measure the ionization current. In general, where the filament is heated by an ac power source, the response speed for temperature control is less than 100 msec since the fluctuation of the voltage frequency is considered to be at most about 10 Hz.

Figure 3:
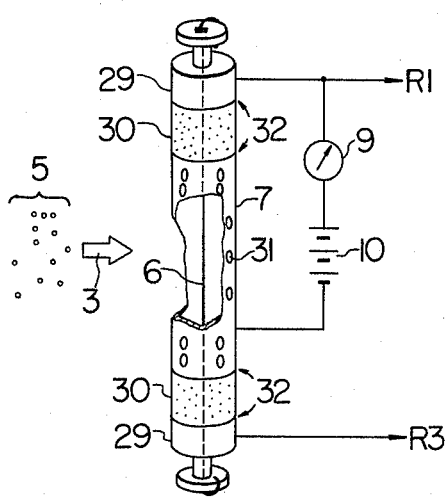
FIG. 3 shows in detail the ion detecting section of the ionization detector shown in FIG. 1.

FIG. 3 shows the solid structure of the sensor section of an ionization detector. The dimensions of the sensor section is as listed in the Table given below. The sensor has a diode structure in principle comprising a platinum filament 6 having a diameter of 0.3 mm and a length of 6 cm and a cylindrical collector 7 having an inner diameter of 8 mm, an outer diameter of 10 mm and a length of 3 cm, the filament 6 and the collector being coaxially arranged. The filament 6 is extended tightly between filament electrodes 29, having its ends anchored to the electrodes 29. The filament 6 is insulated from the collector 7 by means of insulating members 30 (made of $Al_2O_3$). To keep the filament 6 straight so that it may rest coaxial with the collector 7, through holes are cut in the filament electrodes 29 and the insulating members 30. The filament 6 is extended through the through holes. Silver solder is used to connect the filament electrodes 29 with the insulating members 30 and the cylindrical collector 7 with the insulating members 30. The filament electrodes 29 and the collector 7 are both made of alloy, Kovar (trade name), having the same thermal expansion coefficient as that of the insulating member 30 in order to prevent the joined parts from disjoining from each other owing to the difference in thermal expansion between the joined parts during the silver soldering. The collector 7 is provided with 70 holes 31 each having a diameter of 1 mm, through which sampled gas 3 containing sodium particles 5 passes toward the filament 6.

TABLE

| Components | Material | Dimensions |
| --- | --- | --- |
| Filament 5 | Platinum | d = 0.3 mm, l = 60 mm |
| Filament electrode 29 | Kovar | $d_i$ = 1 mm, $d_o$ = 10 mm, l = 5 mm |
| Collector 6 | Kovar | $d_i$ = 8 mm, $d_o$ = 10 mm, l = 30 mm |
| Insulating member 30 | Alumina $Al_2O_3$ | $d_i$ = 1 mm, $d_o$ = 10 mm, l = 5 mm |
| Gas inlet holes 31 | | d = 1 mm | d: diameter,
l: length,
$d_i$: inner diameter
$d_o$: outer diameter.

Figure 4:
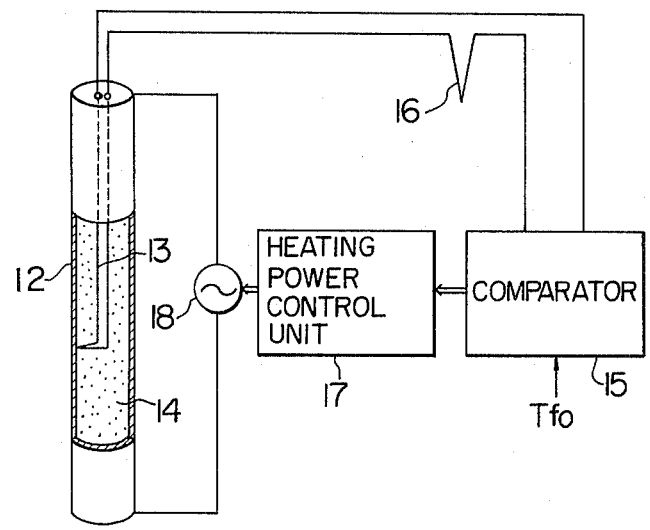
FIG. 4 shows an ionization detector as another embodiment of this invention.

FIG. 4 shows another embodiment of this invention. In this embodiment, the filament is a cylinder of platinum film 12 and a thermocouple 13 for measuring the temperature at the filament is provided within the cylindrical filament. The cylindrical platinum filament 12 has an outer diameter of 2 mm and a length of 50 mm. Insulating material 14 such as $Al_2O_3$ insulates the thermocouple 13 from the filament 12. Current is caused to flow constantly through the filament, i.e. platinum film, to generate joule heat in the filament. The filament 12 is surrounded by a collector 7 (not shown) as in FIG. 1. When some disturbance changes the temperature of the platinum film, the thermocouple 13 immediately detects the temperature change to deliver an output signal to a comparator 15 connected thereto. A thermocouple 16 is used to generate a standard thermal e.m.f. and its contact is usually kept at 0° C. The comparator 15 compares the signal from the thermocouple 13 with the initially set operating temperature $T_{fo}$ of the filament and delivers a signal corresponding to the difference between them to a unit 17 for controlling the power source for heating the filament. In this embodiment, the temperature of the filament is always monitored by the thermocouple 13 and the current flowing through the filament is controlled depending on the temperature of the filament. In order to improve the precision in control, it is desired to use a proportional temperature controller (PID controller) as the filament heating power source control unit 17.

Figure 5:
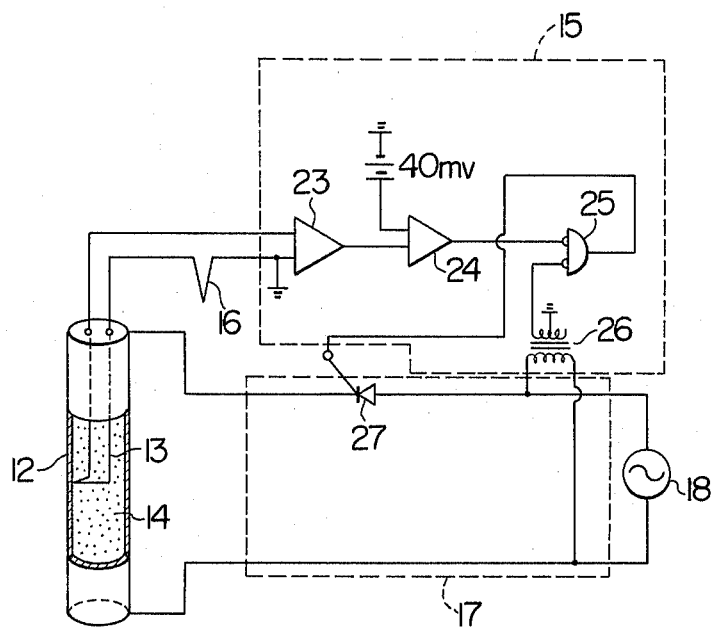
FIG. 5 shows the detailed circuit configuration of the temperature control section shown in FIG. 4.
Figure 6A:
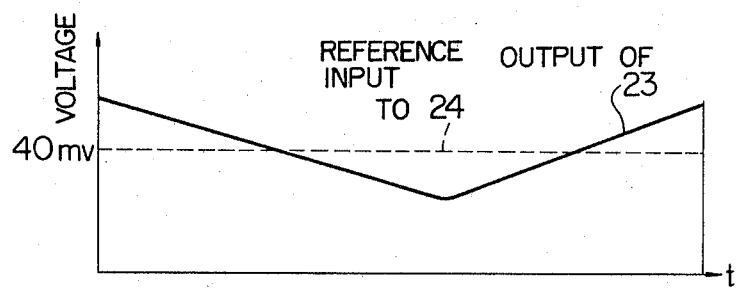
FIGS. 6A to 6D shows the waveforms of signals appearing at several points in FIG. 5.
Figure 6B:
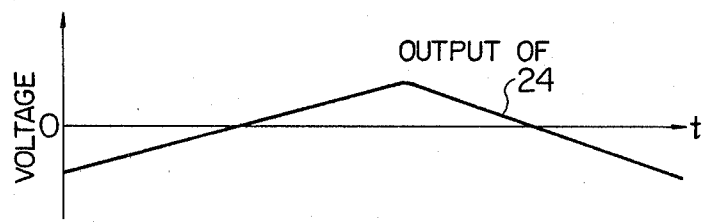
Figure 6C:
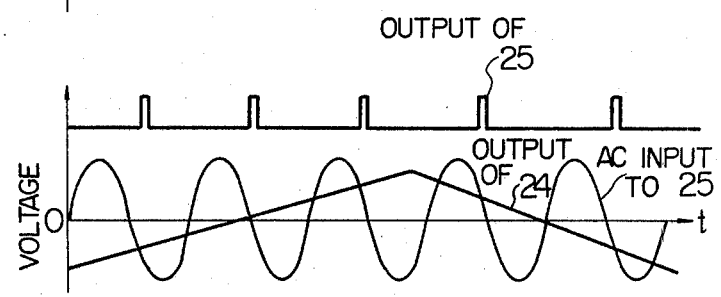
Figure 6D:
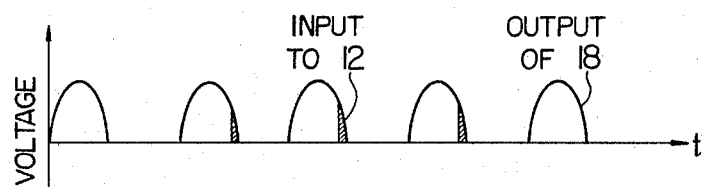

FIG. 5 shows in further detail the circuit shown in FIG. 4. FIGS. 6A to 6D show waveforms appearing at several points in the circuit shown in FIG. 5. The operation of this circuit will be described below with the aid of these figures. In this embodiment, in order to keep the temperature of the filament constant, that temperature is continually monitored and compared with the initially set operating temperature and the current proportional to the difference obtained as a result of the comparison is controlled by an SCR 27 and then fed back to the platinum film 12. The temperature of the platinum film 12 is measured by the thermocouple 13. The output of the thermocouple 13, i.e. signal current, is converted, by an amplifier 23, to the corresponding voltage, which is in turn supplied to a differential amplifier 24. In the differential amplifier 24, the input voltage is compared with a reference input (for example, 40 mV if chromel-alumel thermocouples are used as the thermocouples 13 and 16 and if it is desired to set the filament temperature at 1000° C.) corresponding to the preset temperature and the difference between both the inputs is delivered. (See FIGS. 6A and 6B). The difference voltage obtained from the differential amplifier 24 is supplied to a gate circuit 25 and compared there with the voltage of a filament heating power source (ac source) 18. This voltage of the filament heating power source 18 is usually higher than the output (difference voltage) of the differential amplifier 24 and therefore stepped down by a transformer 26. FIG. 6C shows the state of comparison. The gate circuit 25 is so designed as to generate pulses whenever the ac input to the gate 25, which was obtained by stepping down the voltage of the source 18, becomes smaller in amplitude than the output of the differential amplifier 24. These pulses are supplied to an SCR 27 described later, to control the conduction thereof. Accordingly, as shown in FIG. 6D, the voltage applied to the platinum film 13 has the waveform represented by the shaded areas as parts of the half-wave rectified waveform of the output from the source 18. It is here to be noted that the frequency of the filament heating power source 18 must be higher than the frequency of the fluctuation of the filament temperature. With the circuit described above, even if the filament temperature changes, the current (or power) proportional to the magnitude of the temperature change can be supplied, with high response, to the filament of platinum film. Consequently, the temperature fluctuation can be considerably reduced (within a range of $-1° \sim +1°$ C. for about 1000° C.) as compared with that observed in the conventional detector having no filament temperature controller (about $\pm 50°$ C. for about 1000° C.).

Figure 7:
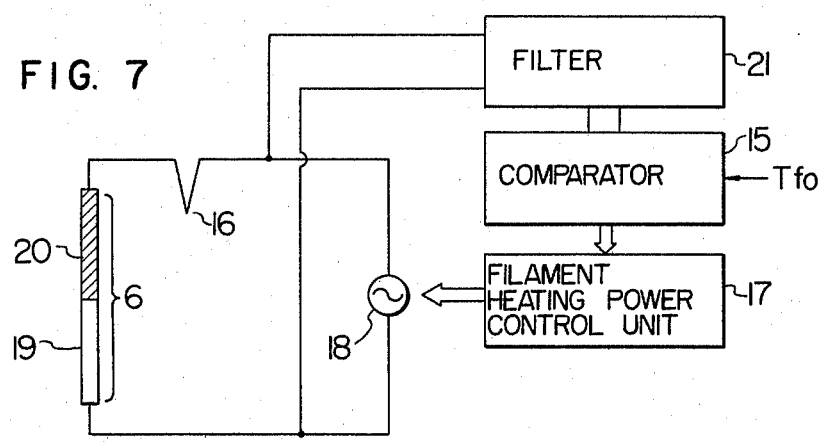
FIG. 7 shows an ionization detector as still another embodiment of this invention.

FIG. 7 shows another embodiment of this invention, which is an improved version of the embodiment shown in FIG. 4. In this improved embodiment, the filament serves also as thermocouple. As already described, the filament of the SID is usually made of platinum and can be preferably used as a counterpart of a platinum vs. platinum-rhodium alloy thermocouple for high temperature measurement. As shown in FIG. 7, a platinum wire 19 is connected with a wire 20 of platinum-rhodium alloy to form a filament 6. The filament 6 is surrounded by a collector electrode (not shown) as in FIG. 1. When current flows through the filament 6, it generates joule heat therein. A thermal e.m.f. is generated between the junction of the filament and a reference thermocouple 16 and the filament temperature can be monitored by using the thermal e.m.f. Usually, the filament is heated by alternating circuit and the induced e.m.f. contains ac components. A filter 21 is used to eliminate such ac noise components and therefore only the thermal e.m.f. corresponding to the filament temperature is applied to a comparator 15. If the frequency of the filament heating ac power source 18 is set high enough, i.e. above 100 Hz, then the elimination of ac noise components by the filter is facilitated.

As described above, according to this invention, the temperature of the filament of the SID can be kept constant and therefore the number of sodium particles can be exactly detected irrespective of the fluctuation of the flow of carrier gas or the current for heating the filament. This invention therefore makes a great contribution to the improvement in the reliability of a sodium leakage detector.

I claim:

1. An ionization detecting element for ionizing a substance to be measured, comprising:
   an insulating member in the form of a rod;
   a filament electrode film provided on the surface of said insulating member; and
   a thermocouple so supported by said insulating member as to be in contact with said filament electrode film.

2. An ionization detector for detecting the number of the ionized particles by ionizing a substance to be measured, comprising: a linear filament electrode for ionizing said substance to be measured;
   a cylindrical collector electrode having plural holes through which said substance to be measured passes, said cylindrical collector electrode being disposed coaxial with said filament electrode;
   a dc power source connected between said filament electrode and said collector electrode;
   a bridge circuit connected with said filament electrode, for detecting the change in the temperature of said filament;
   a heating power source for heating said filament electrode; and
   an amplifier connected with said heating power source, for controlling the temperature of said filament electrode in accordance with the output of said bridge circuit.

3. An ionization detector for detecting the number of ionized particles by ionizing a substance to be measured, comprising:
   an insulating member in the form of a rod;
   a filament electrode film provided on the surface of said insulating member;
   a thermocouple supported by said insulating member, for detecting the temperature of said filament electrode film;
   a cylindrical collector electrode having plural holes through which said substance to be measured passes, said collector electrode being disposed coaxial with said filament electrode film;
   a dc power source connected between said filament electrode film and said collector electrode;
   a heating power source for heating said filament electrode film;
   a comparator for comparing said detected temperature of said filament electrode film with a reference temperature; and a heating power source control unit connected with said heating power source, for controlling the temperature of said filament electrode film in accordance with the output of said comparator.

4. An ionization detector for detecting the number of ionized particles by ionizing a substance to be measured, comprising:
- a thermocouple serving as a filament electrode for ionizing substance to be measured;
- a cylindrical collector electrode having plural holes through which said substance to be measured passes, said collector electrode being disposed coaxial with said thermocouple;
- a dc power source connected between said thermocouple and said collector electrode;
- a heating power source for heating said thermocouple serving as said filament electrode;
- a comparator for comparing the temperature detected by said thermocouple with a reference temperature; and
- a heating power source control unit connected with said heating power source, for controlling the temperature of said thermocouple in accordance with the output of said comparator.

5. An ionization detector comprising:
- a heating means for ionizing the particles of a substance to be measured;
- a collector electrode for collecting said ionized particles;
- a detecting means connected between said heating means and said collector electrode, for detecting the inoization current due to said ionized particles, said detecting means including a power source for heating said heating means, a thermalcouple for detecting the temperature of said heating means, a comparator for comparing the detected temperature of said heating means with a reference temperature, and a heating power source control unit connected with said power source, for controlling the temperature of said heating means in accordance with the output of said comparator; and
- a control means for controlling the temperature of said heating means.

6. An ionization detector as claimed in claim 3, wherein said detecting means comprises:
- a bridge circuit for detecting the change in the temperature of said heating means;
- a power source for heating said heating means; and
- an amplifier connected with said power source, for controlling the temperature of said heating means in accordance with the output signal of said bridge circuit.

7. An ionization detector as claimed in claim 5, wherein said thermocouple serves also as said heating means.

* * * * *